(12) United States Patent
Wollenweber et al.

(10) Patent No.: US 9,078,622 B2
(45) Date of Patent: Jul. 14, 2015

(54) METHOD AND APPARATUS FOR DATA SELECTION FOR POSITRON EMISSION TOMOGRPAHY (PET) IMAGE RECONSTRUCTION

(71) Applicant: General Electric Company, Schenectady, NY (US)

(72) Inventors: Scott David Wollenweber, Waukesha, WI (US); Michael George Bonner, Wauwatosa, WI (US); Michael Joseph Cook, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 162 days.

(21) Appl. No.: 13/800,187

(22) Filed: Mar. 13, 2013

(65) Prior Publication Data

US 2014/0276029 A1  Sep. 18, 2014

(51) Int. Cl.
*A61B 6/00* (2006.01)
*A61B 6/03* (2006.01)

(52) U.S. Cl.
CPC ............... *A61B 6/5288* (2013.01); *A61B 6/037* (2013.01); *A61B 6/466* (2013.01); *A61B 6/5264* (2013.01)

(58) Field of Classification Search
CPC ...... A61B 6/5288; A61B 6/037; A61B 6/466; A61B 6/5264
USPC ............................ 600/407–430; 382/128–132
See application file for complete search history.

(56) References Cited

U.S. PATENT DOCUMENTS

| | | | |
|---|---|---|---|
| 8,060,177 B2 | 11/2011 | Hamill | |
| 8,131,044 B2 | 3/2012 | Wollenweber et al. | |
| 8,379,947 B2 | 2/2013 | Garg et al. | |
| 8,391,573 B2 | 3/2013 | Wollenweber | |
| 8,644,910 B2 * | 2/2014 | Rousso et al. | 600/436 |
| 8,699,771 B2 * | 4/2014 | Wollenweber et al. | 382/131 |
| 8,824,757 B2 * | 9/2014 | Kolthammer et al. | 382/128 |
| 2003/0128801 A1 * | 7/2003 | Eisenberg et al. | 378/19 |
| 2007/0232903 A1 | 10/2007 | Hamill | |
| 2010/0198112 A1 * | 8/2010 | Maad | 600/595 |
| 2011/0116695 A1 * | 5/2011 | Wollenweber et al. | 382/131 |

* cited by examiner

*Primary Examiner* — Sanjay Cattungal
(74) *Attorney, Agent, or Firm* — Dean D. Small; The Small Patent Law Group, LLC (57) ABSTRACT

A method for selecting data to reconstruct a three-dimensional (3D) image of a subject of interest includes acquiring a 3D emission dataset of the subject of interest, acquiring a respiratory signal of the subject of interest, the respiratory signal including a plurality of respiratory cycles, and calculating a respiratory profile using the respiratory signal. The method further includes, for each respiratory cycle, generating a gating window, calculating a minimum total squared difference (TSD) between a plurality of phases in the respiratory profile and the same plurality of phases in the respiratory cycle, and positioning the gating window based on the TSD values calculated, and reconstructing a 3D image using only the emission data within the plurality of gated windows. A system and non-transitory computer readable medium are also described herein.

20 Claims, 7 Drawing Sheets

METHOD AND APPARATUS FOR DATA SELECTION FOR POSITRON EMISSION TOMOGRPAHY (PET) IMAGE RECONSTRUCTION

BACKGROUND OF THE INVENTION

The subject matter disclosed herein relates generally to imaging systems, and more particularly to a method and apparatus for optimizing data selected to reconstruct a Positron Emission Tomography (PET) image.

Multi-modality imaging systems exist that scan using different modalities, for example, PET and Single Photon Emission Computed Tomography (SPECT). During operation, the image quality of the conventional imaging systems may be affected by the motion of the object being imaged. More specifically, imaging artifacts may be produced by movement of the object during image acquisition. Respiratory motion is a common source of involuntary motion in mammals (e.g., people and animals) encountered in medical imaging systems and therefore is also a common source of the imaging artifacts.

One known method for reducing the imaging artifacts is to sort the image data into a plurality of bins. One of the bins is then selected as the reference bin and the remaining bins are then registered to the reference bin. However, the reference bin may not include optimal information for registering the remaining bins. For example, the reference bin may include a fewer number of pixels or pixels having a reduced pixel intensity. Thus, when the remaining bins are registered with the reference bin, the quality of the resultant image may be reduced.

Additionally, a PET imaging procedure may last 2-3 minutes per acquired data at a bed position. Thus, several respiratory cycles of image data are acquired and sorted to contribute to image data for each bin. In general, it is assumed that the respiratory cycles include image data that is repeating for the internal patient anatomy over the respiratory cycles such that image data for each respiratory cycle may be summed into the bins. However, in general the patient's breathing is not consistent over the entire imaging procedure. The methods described herein may be applied independently to any or all such data acquisitions associated with a multi-position ('whole body') scan where respiratory motion is present.

In some methods for reducing the imaging artifacts, the patient may hold their breath during the scan. However, because PET data, for example, may be acquired over several minutes, the patient typically has to breathe several times during the PET acquisition. Thus the patient's breathing results in patient motion which may potentially result in imaging artifacts.

BRIEF DESCRIPTION OF THE INVENTION

In one embodiment, a method for selecting data to reconstruct a three-dimensional (3D) image of a subject of interest is provided. The method includes acquiring a 3D emission dataset of the subject of interest, acquiring a respiratory signal of the subject of interest, the respiratory signal including a plurality of respiratory cycles (the 'respiratory trace'), and calculating a respiratory profile using the respiratory signal. A profile, for instance, may include plotting respiratory displacement as a function of phase for all cycles acquired during data acquisition, followed by a displacement-based calculation based upon a subset of phase locations or phase bins. Such a calculation could include the displacement average for all cycles during each phase bin. The method further includes, for each respiratory cycle, generating a gating window, calculating a minimum total squared difference (TSD) between a plurality of phases in the respiratory profile and the same plurality of phases in the respiratory cycle, and positioning the gating window based on the TSD values calculated, and reconstructing a 3D image using only the emission data within the plurality of gated windows. A system and non-transitory computer readable medium are also described herein.

In another embodiment, an imaging system is provided. The imaging system includes a detector, and a computer coupled to the detector. The computer is programmed to acquire a 3D emission dataset of the subject of interest, acquire a respiratory signal of the subject of interest, the respiratory signal including a plurality of respiratory cycles, and calculate a respiratory profile using the respiratory signal. The computer is further programmed to for each respiratory cycle, generate a gating window, calculate a minimum total squared difference (TSD) between a plurality of phases in the respiratory profile and the same plurality of phases in the respiratory cycle, and position the gating window based on the TSD values calculated, and reconstruct a 3D image using only the emission data within the plurality of gated windows.

In a further embodiment, a non-transitory computer readable medium is provided. The non-transitory computer readable medium is encoded with a program programmed to instruct a computer to acquire a 3D emission dataset of the subject of interest, acquire a respiratory signal of the subject of interest, the respiratory signal including a plurality of respiratory cycles, and calculate a respiratory profile using the respiratory signal. The non-transitory computer readable medium also instructs a computer to, for each respiratory cycle, generate a gating window, calculate a minimum total squared difference (TSD) between a plurality of phases in the respiratory profile and the same plurality of phases in the respiratory cycle, and positioning the gating window based on the TSD values calculated, and reconstruct a 3D image using only the emission data within the plurality of gated windows.

DETAILED DESCRIPTION OF THE INVENTION

The foregoing summary, as well as the following detailed description of various embodiments, will be better understood when read in conjunction with the appended drawings.

To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments described herein provide a method and system for selecting data to reconstruct a three-dimensional (3D) image. In various embodiments, the method includes acquiring a 3D emission dataset of the subject of interest, acquiring a respiratory signal of the subject of interest, the respiratory signal including a plurality of respiratory cycles, and calculating a respiratory profile using the respiratory signal. The method further includes for each respiratory cycle, generating a gating window, calculating a total squared difference (TSD) between a plurality of phases in the respiratory profile and the same plurality of phases in the respiratory cycle, and repositioning the gating window such that the TSD is reduced or minimized and a 3D image is reconstructed using only the emission data within the plurality of gated windows.

Figure 1:
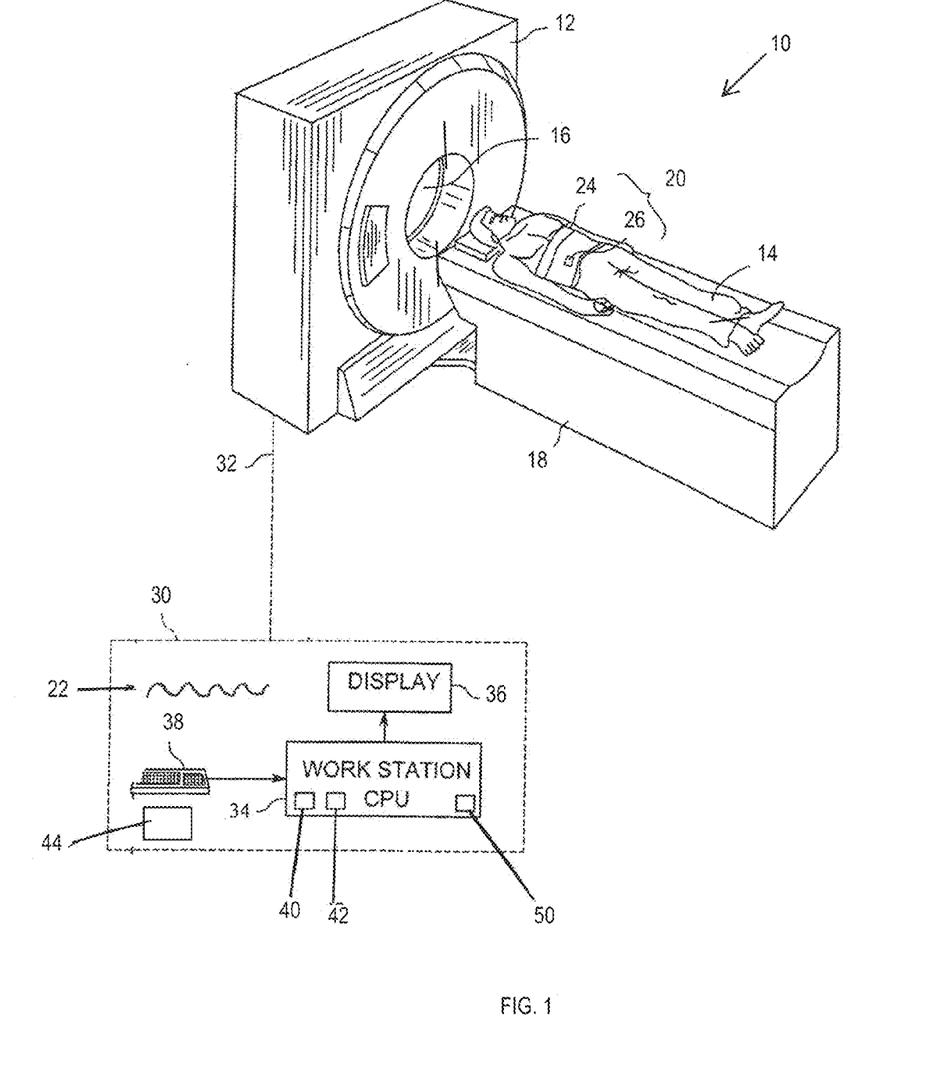
FIG. 1 is a pictorial illustration of an exemplary imaging system formed in accordance with various embodiments.

FIG. 1 is an imaging system 10 that may be utilized to implement the various methods described herein. In the illustrated embodiment, the imaging system 10 is a stand-alone Positron Emission Tomography (PET) imaging system. Optionally, the imaging system 10 may be embodied, for example, as a stand-alone Single Photon Emission Computed Tomography (SPECT) system. The various embodiments described herein are not limited to standalone imaging systems. Rather, in various embodiments, the imaging system 10 may form part of a multi-modality imaging system that includes the PET imaging system 10 and a CT imaging system, a Magnetic Resonance Imaging (MRI) system, or a SPECT system, for example. Moreover, the various embodiments are not limited to medical imaging systems for imaging human subjects, but may include veterinary or non-medical systems for imaging non-human objects, etc.

Referring to FIG. 1, the imaging system 10 includes a gantry 12. The gantry 12 includes a detector 312 (shown in FIG. 8) that is configured to acquire emission data. During operation, a patient 14 is positioned within a central opening 16 defined through the gantry 12, using, for example, a motorized table 18. The imaging system 10 may also include at least one motion sensor 20 that is adapted to detect and transmit information that is indicative of the motion of the patient 14. In the illustrated embodiment, the motion sensor 20 is a respiratory motion sensor that is configured to generate a respiratory signal 22 that provides information of the respiratory motion of the patient 14 during an imaging procedure. In one embodiment, the motion sensor 20 may be embodied as a belt-type motion sensor 24 that is adapted to extend at least partially around the patient 14. Optionally, the motion sensor 20 may be embodied as a motion sensor 26 that is adapted to be secured to a predetermined position on the patient 14. It should be realized that although two different motion sensors 20 are described, the imaging system 10 may include other types of motions sensors 20 to generate motion related information of the patient 14.

The imaging system 10 also includes an operator workstation 30. During operation, the motorized table 18 moves the patient 14 into the central opening 16 of the gantry 12 in response to one or more commands received from the operator workstation 30. The operator workstation 30 then positions both the gantry 12 and the table 18 to both scan the patient 14 and acquire an emission dataset 40 of the patient 14. The workstation 30 may be embodied as a personal computer (PC) that is positioned near the imaging system 10 and hard-wired to the imaging system 10 via a communication link 32. The workstation 30 may also be embodied as a portable computer such as a laptop computer or a hand-held computer that transmits information to, and receives information from, the imaging system 10. Optionally, the communication link 32 may be a wireless communication link that enables information to be transmitted to or from the workstation 30 to the imaging system 10 wirelessly. In operation, the workstation 30 is configured to control the operation of the imaging system 10 in real-time. The workstation 30 is also programmed to perform medical image diagnostic acquisition and reconstruction processes described herein.

In the illustrated embodiment, the operator workstation 30 includes a central processing unit (CPU) or computer 34, a display 36, an input device 38, and a memory device 44. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 34 executes a set of instructions that are stored in one or more storage elements or memories, in order to process information, such as the emission dataset 40, received from the detector 312. The storage elements may also store data or other information as desired or needed. The storage element may be in the form of an information source or a physical memory element located within the computer 34.

In operation, the computer 34 connects to the communication link 32 and receives inputs, e.g., user commands, from the input device 38. The input device 38 may be, for example, a keyboard, mouse, a touch-screen panel, and/or a voice recognition system, etc. Through the input device 38 and associated control panel switches, the operator can control the operation of the PET imaging system 10 and the positioning of the patient 14 for a scan. Similarly, the operator can control the display of the resulting image on the display 36 and can perform image-enhancement functions using programs executed by the computer 34.

The imaging system 10 also includes a data selection module 50 that is configured to implement various methods described herein. The module 50 may be implemented as a piece of hardware that is installed in the computer 34. Optionally, the module 50 may be implemented as a set of instructions that are installed on the computer 34. The set of instructions may be stand alone programs, may be incorporated as subroutines in an operating system installed on the computer 34, may be functions in an installed software package on the computer 34, and the like. It should be understood that the various embodiments are not limited to the arrangements and instrumentality shown in the drawings.

The set of instructions may include various commands that instruct the module 50 and/or the computer 34 as a processing machine to perform specific operations such as the methods and processes of the various embodiments described herein. The set of instructions may be in the form of a non-transitory computer readable medium. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
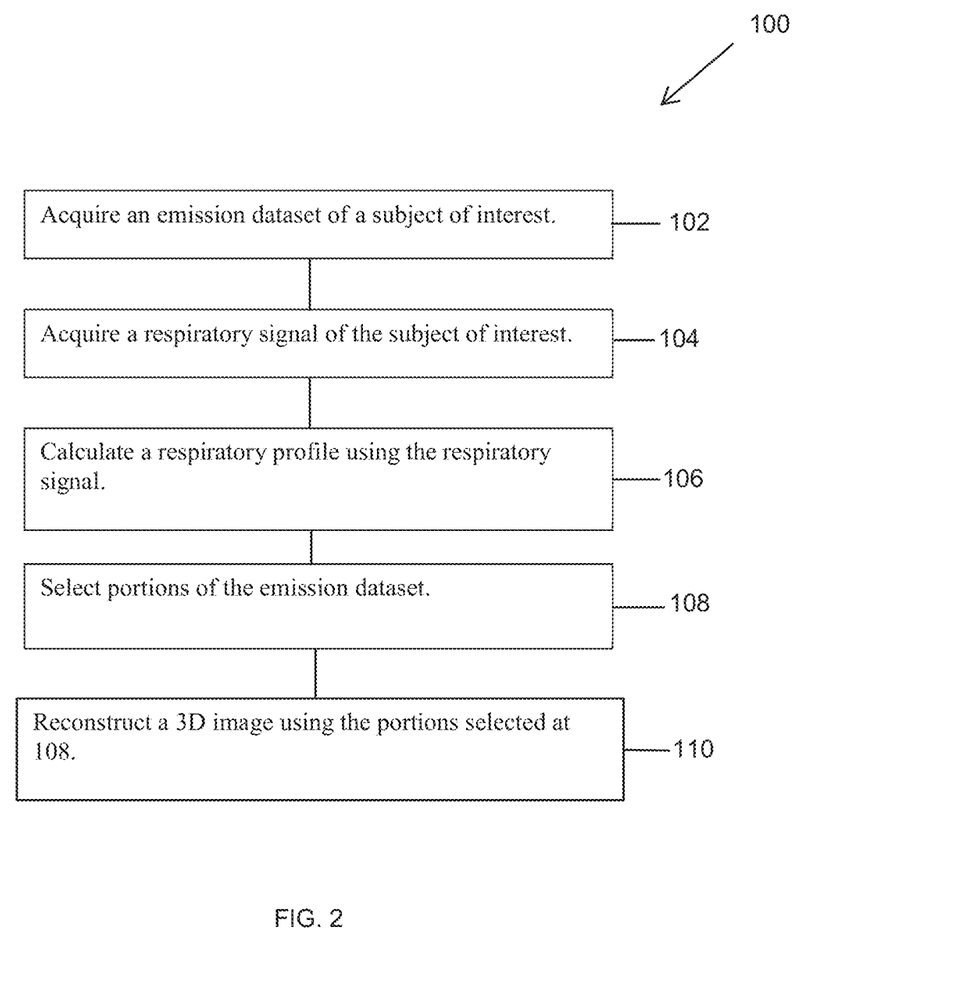
FIG. 2 is a flowchart illustrating a method for selecting data utilized to reconstruct a three-dimensional (3D) image in accordance with various embodiments.

FIG. 2 is a simplified block diagram of an exemplary method 100 that may be utilized to perform data selection and image reconstruction. In various embodiments, the method 100 may be utilized to automatically select portions of the emission dataset 40 acquired during a scan of the patient 14 and to reconstruct an image of the patient 14 using the selected portions. In the exemplary embodiment, the method 100 may be implemented using the computer 34 and/or the data selection module 50 (shown in FIG. 1). The method 100 may therefore be provided as a non-transitory computer-readable medium or media having instructions recorded thereon for directing the computer 34 and/or the data selection module 50 to perform an embodiment of the methods described herein. The medium or media may be any type of CD-ROM, DVD, floppy disk, hard disk, optical disk, flash RAM drive, or other type of computer-readable medium or a combination thereof.

Referring to FIG. 2, at 102 an emission dataset, such as the emission dataset 40 (shown in FIG. 1) is acquired. In the exemplary embodiment, the emission dataset 40 may be acquired using the PET imaging system 10 (shown in FIG. 1). For example, the emission dataset 40 may be acquired by performing a scan of a patient 14 to produce the emission dataset 40. Optionally, the emission dataset 40 may be acquired from data collected during a previous scan of the patient 14, wherein the emission dataset 40 has been stored in a memory, such as a memory device 44 (shown in FIG. 1). The emission dataset 40 may be stored in any format, such as a list mode dataset, for example. The emission dataset 40 may be acquired during real-time scanning of the patient 14. For example, the methods described herein may be performed on emission data as the emission dataset 40 is received from the PET imaging system 10 during a real-time examination of the patient 14.

At 104, information indicative of motion of the patient 14 is acquired. The motion information may be acquired during a real-time scan of the patient 14, during a related PET imaging scan, or during any other medical imaging system scanning procedure. Optionally, the motion information may be acquired from a database of previous medical examination information or may be derived from other data acquired during the scan, such as the raw emission data. In various embodiments, the motion information is embodied as the respiratory signal 22, acquired using the motion sensor 20 shown in FIG. 1. Optionally, the motion information may be acquired from information saved in a memory device located in the computer 34. In the exemplary embodiment, the motion information is representative of the respiratory motion of the patient 14 within a selected volume of interest. Optionally, the motion information may be embodied as a cardiac signal.

At 106, a respiratory profile is calculated using the respiratory signal 22 acquired at 104. In various embodiments, the respiratory signal 22 includes a plurality of respiratory cycles. As used herein, a respiratory cycle includes an inspiration phase and an expiration phase. Thus, it should be realized that during a typical scanning procedure, the patient 14 may inhale and exhale numerous times such that the respiratory signal 22 includes a plurality of individual respiratory cycles each having an inspiration phase and an expiration phase.

Figure 3:
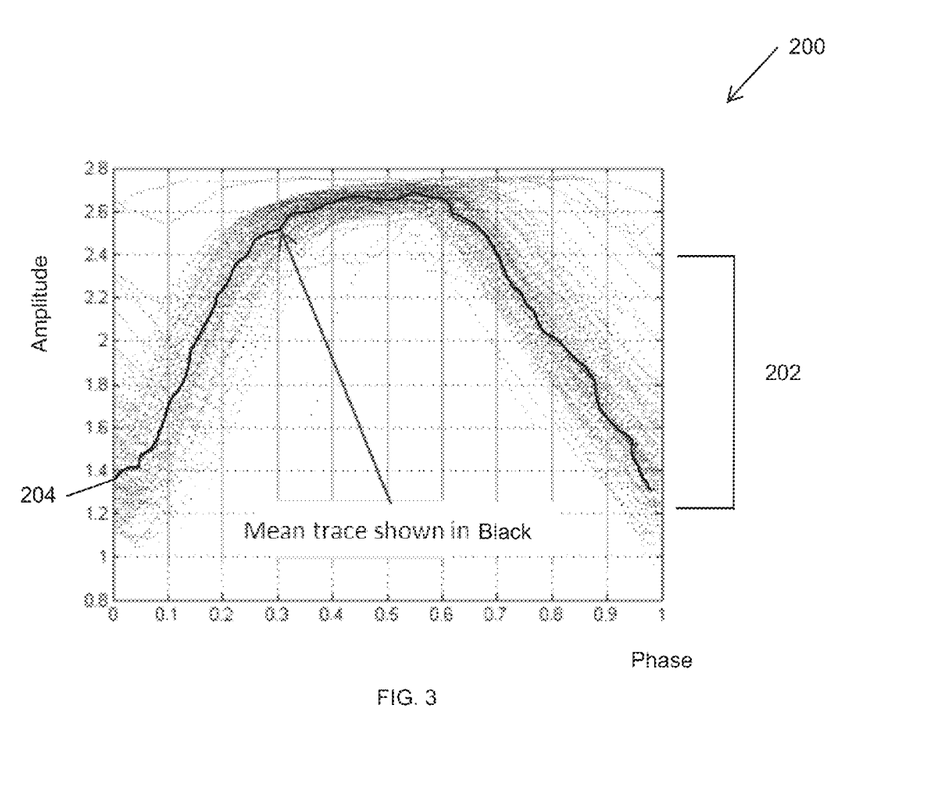
FIG. 3 is a graphical illustration of a plurality of respiratory cycles that may be generated in accordance with various embodiments.

For example, FIG. 3 is a graphical illustration 200 of an exemplary respiratory signal, such as the respiratory signal 22, shown in FIG. 1 that has been divided into a plurality of individual respiratory cycles 202. The x-axis represents the phase of the respiratory cycles 202 and the y-axis represents the amplitude of the breathing cycles 202. In the illustrated embodiment, the respiratory cycles 202 are arranged such that an inspiration phase of each respiratory cycle 202 is substantially aligned with the inspiration phase of the remaining respiratory cycles 202. It should be realized that FIG. 3 is an exemplary graphical illustration of the individual respiratory cycles 202 to enable the reader to better understand the various embodiments described herein and in various embodiments, the respiratory cycles 202 are not graphically plotted as shown in FIG. 3.

As described above, at 106 a respiratory profile 204, shown in FIG. 3, is calculated using the respiratory signal 22. In various embodiments, the respiratory profile 204 is calculated by determining a mean value for each phase in the N respiratory cycles 202. For example, assume that the respiratory cycles 202 are each divided into M phases. Moreover, assume that for phase $M_1$, the amplitude of a respiratory cycle $N_1$ is 4, the amplitude of a respiratory cycle $N_2$ is 6, and the amplitude of a respiratory cycle $N_3$ is 8. Thus, the mean of the respiratory cycles 202 at the phase $M_1$ is 6. Accordingly, the respiratory profile 204 represents the mean values calculated at each of the respiratory phases M for the plurality of respiratory cycles 202.

Figure 4:
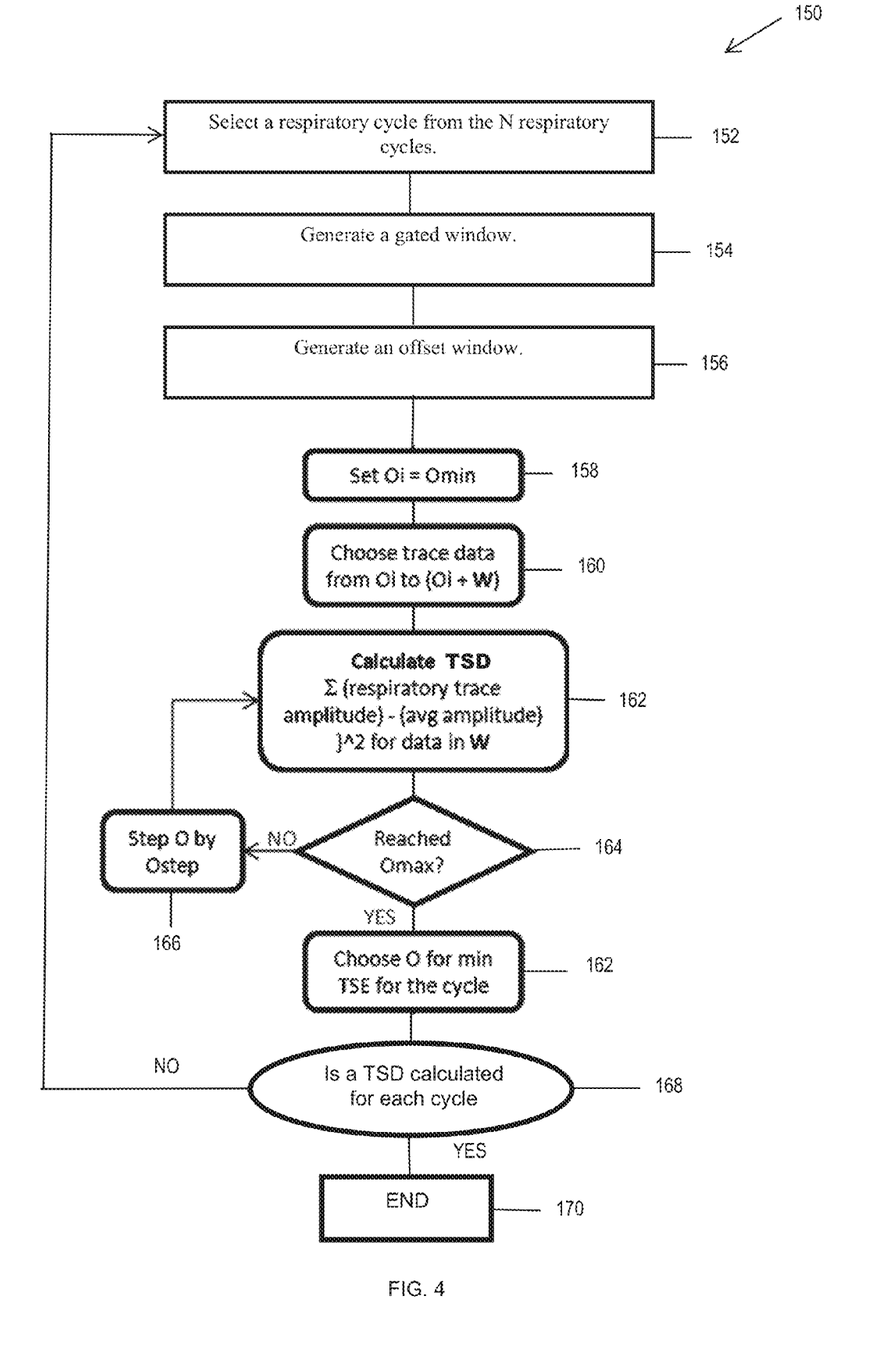
FIG. 4 is a flowchart illustrating a portion of the method shown in FIG. 2 in accordance with various embodiments.

Referring again to FIG. 2, at 108 portions of the emission dataset 40 are selected. FIG. 4 is a flowchart of a method 150 of selecting portions of the emission data at 108. In various embodiments, a portion of emission data is selected from emission data corresponding to each of the N respiratory cycles 202. Thus, N portions of emission data are selected at 108. In various embodiments, each of the N portions of the emission dataset 40 is selected by analyzing each respiratory cycle 202 individually. Thus, while steps 152-170 are described with respect to a single respiratory cycle, it should be realized that steps 152-170 are repeated iteratively until emission data corresponding to some or all of the plurality of respiratory cycles 202 is selected.

Figure 5:
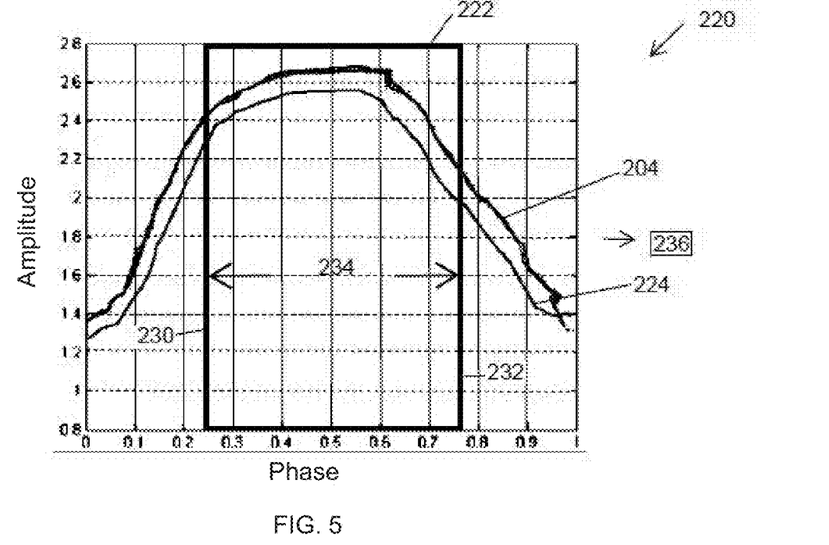
FIG. 5 is a graphical illustration of a gating window that may be generated in accordance with various embodiments.

Accordingly at 152 a first respiratory cycle, such as a respiratory cycle 224 shown in FIG. 5, is selected from the plurality of respiratory cycles 202. At 154 a gated window is generated for the respiratory cycle 224. For example, FIG. 5 is a graphical illustration 220 of an exemplary gated window 222 that may be generated for the respiratory cycle 224 that is a portion of the plurality of N respiratory cycles 202 described above. In various embodiments, the gated window 222 has a first side 230, a second side 232, and a width 234. In operation, the gated window 222 is utilized to select a portion 236 of the emission dataset 40 that is utilized to reconstruct a 3D image of the patient 14, such as a 3D image 42 shown in FIG. 1. More specifically, it should be realized that the respiratory signal 22 is registered with the emission dataset 40 such that particular emission data within the emission dataset 40 may be identified using the respiratory signal 22. Therefore, it should be further realized that each respiratory cycle 202 forming the respiratory signal 22 is also registered with a portion of the emission dataset 40.

In various embodiments, the width 234 of the gated window 222 may be manually selected by a user based on apriori information. More specifically, various embodiments described herein are utilized to select emission data, e.g. emission data within the gated window 222, that is relatively unaffected by respiratory motion. The selected emission data, e.g. the portion 236, may then be utilized to reconstruct a 3D image of the patient 14. The remaining emission data, e.g. the emission data that is outside the gated window 222 is therefore not utilized to reconstruct the image.

Thus, in various embodiments, the user may manually increase the width 234 of the gated window 222 such that more emission data is selected and utilized to reconstruct the 3D image or reduce the width 234 such that less emission data is selected and utilized to reconstruct the 3D image. For example, assume that the user sets the width 234 of the gated window 222 to 50% of the respiratory cycle. In operation, 50% of the emission data registered with the respiratory cycle 224 is then selected and utilized to reconstruct the 3D image. Similarly, if the user sets the width 234 of the gated window 222 to 40%, then 40% of the emission data registered with the respiratory cycle 224 is then selected and utilized to reconstruct the 3D image. In various embodiments, the width 234 of the gated window 222 may be automatically set by the imaging system 10. Moreover, the user may then manually adjust the width 234 during operation. It should be realized that the width 234 of the gated window 222 generated at 154 may be the same for each of the respiratory cycles 202 or may be different for various respiratory cycles 202. For example, the gated window 222 generated for the respiratory cycle 224 may have a width 234 that is different that a width of a gated window (not shown) generated for a different respiratory cycle (not shown). In the exemplary embodiment, the width of the gated window generated at 154 is the same for each of the respiratory cycles 202.

Figure 6:
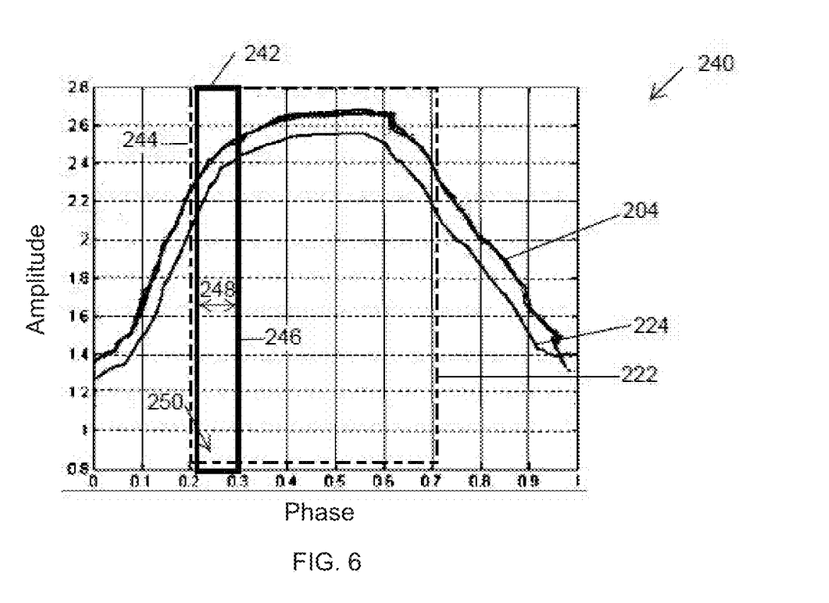
FIG. 6 is a graphical illustration of an window of phase offset values that may be generated in accordance with various embodiments.

As described above, the gated window 222 is utilized to select emission data within the respiratory cycle 224. Accordingly, it is desirable to position the gated window 222 such that emission data that is least affected by motion is selected by the gated window 222 and then utilized to reconstruct the 3D image. Therefore, and referring again to FIG. 4, at 156 an offset window 242, shown in FIG. 6, is generated. In operation, the offset window 242 is utilized to identify a position or phase to initiate emission data selection. More specifically, in operation, the offset window 242 is utilized to position the gated window 222 such that the first side 230 of the gated window 222 is positioned at the position identified by the offset window 242.

For example, FIG. 6 is a graphical illustration 240 of the exemplary offset window 242 that may be generated for the respiratory cycle 224 described above. The offset window 242 is defined by a first side 244 ($O_{min}$), a second side 246 ($O_{max}$), and a width 248.

In various embodiments, the width 248 of the offset window 242 may be manually selected by a user or automatically set by the imaging system 10. Thus, in various embodiments, the user may manually increase the width 248 of the offset window 242 such that a larger portion of the respiratory cycle 224 is analyzed or reduce the width 248 such that smaller portion of the respiratory cycle 224 is analyzed. For example, assume that the user sets the width 248 of the offset window 242 to 10%, e.g. 10% of the total respiratory cycle 224. Moreover, assume that the user positions the offset window 242 to analyze the respiratory phases between 20% and 30% of the respiratory cycle 224. In operation, the offset window 242 is then configured to analyze a plurality of steps ($O_{step}$) 250, or phases, within the offset window 242 to identify a location of the respiratory cycle 224 that includes the least motion. In various embodiments, the size of the steps 250 may be set to, for example 1%, such that 10 phase offset increments are examined within the offset window 242, e.g. the offset window 242 has a width of 10%. In another example, the size of the steps 250 may be any value, such as 0.5% such that 20 different steps 250 or phase offset increments are analyzed within the offset window 242, etc.

Referring again to FIG. 4, to analyze the information within the gating window 222 using the offset window 242, at 158 an initial offset point ($O_i$) is set equal to $O_{min}$. More specifically, the computer 34 and/or the module 50 is programmed to initiate the analysis of the respiratory cycle 224 at the first side 244 of the offset window 242 as shown in FIG. 6. In the illustrated embodiment, the first side 244 of the offset window 242 is positioned at the 20% phase point. Referring again to FIG. 4, at 160 the data within the width 222 of the gating window 236 is selected as described above. Thus, in the illustrated embodiment, the computer 34 and/or the module 50 are configured to analyze the respiratory cycle 224 between 20% and 70% of the respiratory cycle 224 as shown in FIG. 6.

At 162 the computer 34 and/or the module 50 is programmed to generate a total squared difference (TSD) for data within the gated window 222 with the offset 244 at each step 250 in the offset window 242. Therefore, a TSD value at the initial offset point ($O_i$) is initially calculated. In various embodiments, the TSD is calculated in accordance with:

$$TSD_{Oi} = (RespiratoryCycleAmplitude_{Oi} - SignalProfile_{Oi})^2$$

In operation, the equation above is a sum of all the data points within the gated window 222, starting at $O_i$ (20% in the example) and extending by the gated window width 234 to 70% (for a 50% gated window in the example). The data within the gated window 222 are used in the summation.

Accordingly, the TSD value at step $O_i$ is initially calculated. At 164 the computer 34 and/or the module 50 determines if a TSD value has been calculated for each step 250 in the offset window 242. For example, in the exemplary embodiment, the offset window 242 has a width of 10%, e.g. $O_{max}$ is equal to $O_{min}+10\%$, and the step size is set to 1%. Accordingly, in the exemplary embodiment, 10 TSD values are calculated for the respiratory cycle 224. Thus, at 164 the computer 34 and/or the module 50 determines if 10 TSD values have been calculated. In one embodiment, if each of the TSD values have not been calculated, then at 166 the computer 34 and/or the module 50 determines the offset value 244 for the next step, e.g. $O_2$, etc. In the exemplary embodiment, at 166 the steps are incremented until a TSD has been calculated using gated window data 222 for each step 250 in the offset window 242. When a TSD value has been calculated for each step 250, then at 168 the computer 34 and/or the module 50 determines the offset corresponding to a TSD value having the lowest value, e.g. the smallest difference between the respiratory cycle amplitude and the average respiratory signal amplitude 204.

At 170 the computer 34 or module 50 determines if a minimum TSD value, which may be within a predefined tolerance, has been calculated for each respiratory cycle in the plurality of respiratory cycles 202. In one embodiment, if a TSD value has been calculated for each respiratory cycle in the plurality of respiratory cycles 202 the method 150 proceeds to step 110 shown in FIG. 2. Optionally, if a TSD value has not been calculated for each respiratory cycle in the plurality of respiratory cycles 202, a subsequent respiratory cycle is selected and the method proceeds to step 152 wherein a subsequent respiratory cycle is selected. It should be realized that steps 152-170 are iteratively repeated until a TSD value is calculated for each respiratory cycle in the plurality of respiratory cycles 202.

Referring again to FIG. 2, at 110 the emission data associated with the portions selected at 168 are utilized to reconstruct a 3D PET image, such as the 3D PET image 42 shown in FIG. 1.

Figure 7:
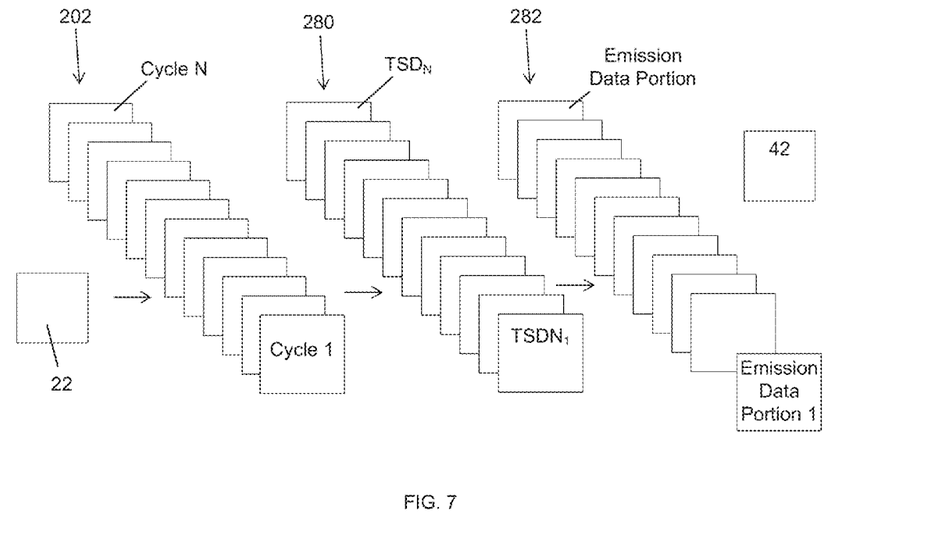
FIG. 7 is a block diagram of a portion of the method shown in FIG. 2 in accordance with various embodiments.

FIG. 7 is simplified block drawing illustrating the method 100 described above. As described above, the respiratory signal 22 is initially divided into a plurality of respiratory cycles 202. A gating window 222 is defined for each respiratory cycle 202. A minimum TSD value 280 is calculated for each respiratory cycle 202. This minimum TSD value has a known corresponding offset from which it was produced. For each respiratory cycle 202, a portion 282 of the emission dataset 40 registered with the gating window 222 using the known offset which produced the minimum TSD, is extracted from the emission dataset 40. The extracted portions 282 are then utilized to reconstruct a 3D PET image 42. Optionally, if the offset for a given respiratory cycle, produces a minimum TSD that is substantially different than the average TSD's generated from the other data selected in 282, the data may be rejected and therefore not utilized to reconstruct the image 42. More specifically, an average TSD value may be calculated and if the TSD value for a particular cycle is less than a predetermined distance from the average TSD, the data may be rejected. It should be realized that the methods described herein may be applied recursively—the respiratory profile can be re-calculated after rejection and a new rejection criteria applied.

Figure 8:
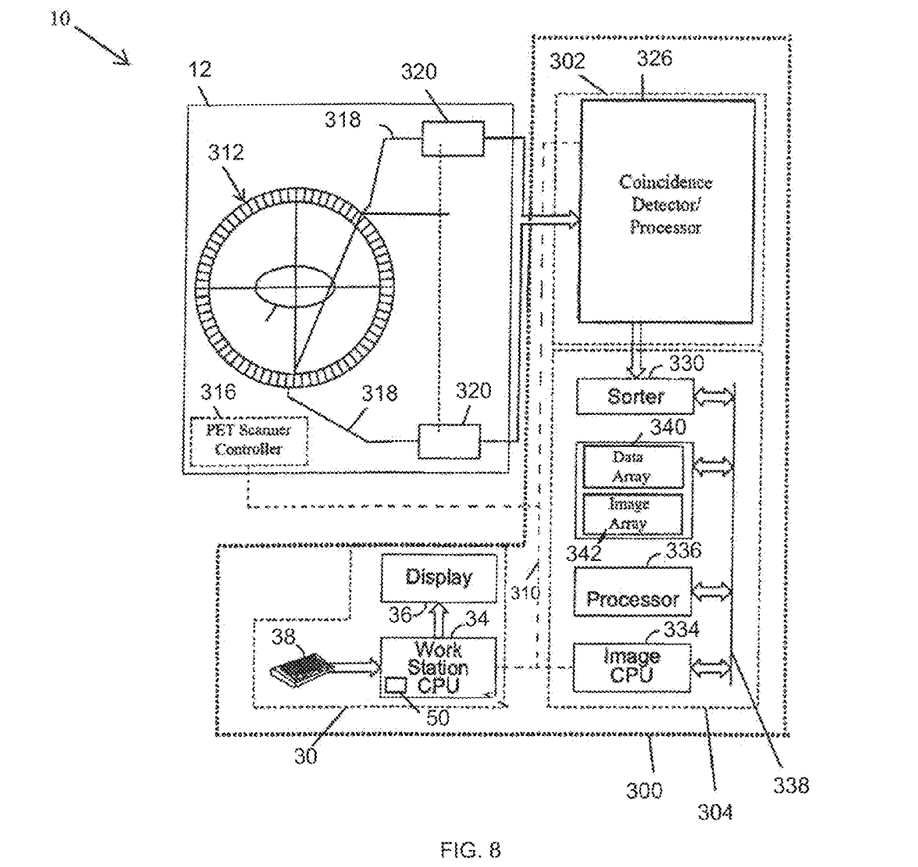
FIG. 8 is a block schematic diagram of a portion of the imaging system illustrated in FIG. 1.

FIG. 8 is a schematic block diagram of the imaging system 10 (shown in FIG. 1). As described above, the imaging system 10 is embodied as a PET imaging system and includes the gantry 12. The PET imaging system 10 also includes a controller 300 to control image reconstruction processes. The controller 300 includes the operator workstation 30. As described above, the operator workstation 30 includes the computer 34, the display 36 and the input device 38. The controller 300 includes a data acquisition processor 302 and an image reconstruction processor 306. The gantry 12, the operator workstation 30, the data acquisition processor 302 and the image reconstruction processor 304 are interconnected via a communication link 310 (e.g., a serial communication or wireless link). In operation, scan data is acquired and transmitted to the data acquisition processor 304. The data acquired by data acquisition processor 302 is reconstructed using image reconstruction processor 304.

The PET imaging system 10 may include, for example, a plurality of detector rings. One such detector ring, detector ring 312, is illustrated in FIG. 8. The detector ring 312 includes a central opening, in which an object 414 (e.g., the patient 14) may be positioned, using, for example, the motorized table 18. The motorized table 18 moves the object 314 into the central opening of detector ring 312, in response to one or more commands received from operator workstation 30. A PET scanner controller 316, also referred to as a gantry controller, is provided (e.g., mounted) in the gantry 12. The PET scanner controller 316 responds to the commands received from the operator workstation 30 through the communication link 310. Therefore, the operation of the PET imaging system 10 is controlled from the operator workstation 30 through the PET scanner controller 316.

In various embodiments, the detector ring 312 includes a plurality of detector elements for performing a PET scan of the object 214. For example, there may be 420 crystals per ring and 24 rings in the scanner. As shown in FIG. 8, the detector ring 312 includes a first detector element 317, a second detector element 319, and several other detectors. It should be noted that the detector elements are referred to as the first detector element and the second detector element, only to differentiate location in FIG. 8. The first detector element 317, like the other detectors, includes a set of scintillator crystals arranged in a matrix that is disposed in front of a plurality of photosensors. When a photon collides with a crystal on a detector, the photon produces a scintilla on the crystal. Each photosensor produces an analog signal on a communication line 318 when a scintillation event occurs. A set of acquisition circuits 320 is provided to receive these analog signals. The acquisition circuits 320 include analog-to-digital converters to digitize analog signals, processing electronics to quantify event signals and a time measurement unit to determine time of events relative to other events in the system. For example, this information indicates when the event took place and the identity of the scintillation crystal that detected the event. The acquisition circuits 320 produce digital data indicating the location, time and total energy of the event. This event data is transmitted through a communication link, for example, a cable, to a coincidence detector or processor 326.

The coincidence detector 326 receives the event data packets from the acquisition circuits 320 and determines if any two of the detected events are in coincidence. In this context, the coincidence is determined by a number of factors. First, the time markers in each event data packet must be within a predetermined time period, for example, 6 ns, of each other. Secondly, the LOR formed by a straight line joining the two detectors that detect the coincidence event should pass through the field of view in detector 312. Events that cannot be paired are discarded. Coincident event pairs are recorded as a coincidence data packet that is communicated through a communication link to a sorter 330 in the image reconstruction processor 304.

The image reconstruction processor 304 includes the sorter 330, a memory module 332, an image CPU 334, an array processor 336, and a back-plane bus 338. The sorter 330 counts all events that occur along each projection ray and organizes them into a coincidence data set. In one embodiment, this data set is organized as a data array 340, referred to as a sinogram. The data array 340 is stored in the memory module 332. The back-plane bus 338 is linked to the communication link 310 through the image CPU 334, which controls communication through the back-plane bus 338. The array processor 336 is also connected to the back-plane bus 338, receives the data array 340 as an input, and reconstructs images in the form of the image arrays 342. The resulting image arrays 342 are stored in the memory module 332.

The images stored in the image array 342 are communicated by the image CPU 334 to the operator workstation 30. The computer 34 is configured to process the scan data received from the detector elements. The scan data includes, for example, sinogram and timing information that is received by controller 300 from the detector elements during an imaging scan. The timing information in one embodiment is the difference in time at which two photons emitted in an annihilation event are detected by detector elements. The timing information may include time stamp information relating to a measured photon event detected by a pair of detector elements, for example, the first detector element 317 and the second detector element 319, for the PET system 10. The time stamp information is the time at which each photon is detected by a detector element, which in various embodiments.

Described herein are various methods and system for selection data to reconstruct a 3D image. The various embodiments described herein enable users to determine the binning parameters, e.g. optimal parameters, to apply prospectively (via protocol) to the collected emission data, based upon patient population. More specifically, the various methods enable analysis of data where a respiratory trace, the measurement of a displacement versus time over one or more respiratory cycles made during the data acquisition, is available and the results may then be applied to the data collected or as a default protocol for data to be collected in the future on a similar patient population. In particular, at least one embodiment generates only a 3D PET image volume using trigger-based respiratory gating (phase) and an offset and window width as two parameters applied over the dataset.

More specifically, an amplitude of a plurality of respiratory cycles is utilized to generate an 'average' or 'mean' amplitude trace that is then utilized to determine the range of respiratory data given a percent window width (amount of PET data to include, e.g. 50%) such that for each cycle, the range within the window minimizes the amplitude, and by extension, the motion impact of respiration on the PET image data.

At least one embodiment enables analysis across patients as well as within a patient to determine the optimal data to include in a 'motion minimized' 3D data volume thus forming the optimal PET image quality from a motion blur perspective. Another embodiment enables a user to determine whether a default set of parameters is 'sufficient' for the operators' purposes, thus potentially avoiding the need to analyze every single scan. Additionally, at least one embodiment may be used during an initial 'testing period' where a user collects data to analyze their parameter choice, but eventually becomes comfortable with application of a default set of parameters based upon measured real patient data and analyzed with the disclosed methods.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodi-

What is claimed is:

1. A method air selecting data to reconstruct a three-dimensional (3D) image of a subject of interest, said method comprising:
    acquiring a 3D emission dataset of the subject of interest;
    acquiring a respiratory signal of the subject of interest, the respiratory signal including a plurality of respiratory cycles;
    calculating a respiratory profile using the respiratory signal;
    for each respiratory cycle, generating a gating window, calculating a minimum total squared difference (TSD) between a plurality of phases in the respiratory profile and the same plurality of phases in the respiratory cycle, and positioning the gating window based on the TSD values calculated; and
    reconstructing a 3D image using only the emission data within the plurality of gating windows.

2. The method of claim 1, wherein the emission data used to reconstruct the 3D image includes 50% or less of the acquired 3D emission dataset for each respiratory cycle, further comprising, for each respiratory cycle, positioning the gating window using information derived from an offset window.

3. The method of claim 2, wherein the offset window further comprises a plurality of steps, said method further comprising, for each respiratory cycle, calculating the TSD values for each step in the offset window; and selecting the minimum TSD value from the calculated TSD values.

4. The method of claim 1, further comprising;
    generating an offset window;
    dividing the offset window into a plurality of steps;
    determining a TSD for each of the plurality of steps;
    selecting the minimum TSD from the plurality of determined TSDs; and
    positioning the gating window at the selected minimum TSD.

5. The method of claim 1, further comprising:
    generating an offset window;
    determining a plurality of TSDs within the offset window; and
    positioning a first side of the gating window at the minimum TSD.

6. The method of claim 1, wherein calculating the respiratory profile comprises:
    generating a plurality of respiratory cycles; and
    calculating a mean value of the plurality of respiratory cycles.

7. The method of claim 1, wherein the plurality of gating windows includes only a single gating window from each respiratory cycle, and wherein, for each respiratory cycle, the single gating window has a first side, a second side, and a width, the width being less than a length of the respiratory cycle.

8. The method of claim 1, further comprising
    determining an average TSD value;
    comparing the TSD values to the average TSD value; and
    rejecting data based on the comparison, wherein the rejected data is not used for reconstructing the 3D image.

9. The method of claim 1, further comprising:
    acquiring a 3D Positron Emission Tomography (PET) dataset of the subject of interest; and
    reconstructing a 3D PET image using a portion of the PET dataset.

10. An imaging system comprising:
    a detector; and
    a computer coupled to the detector, the computer being programmed to:
      acquire a 3D emission dataset of the subject of interest;
      acquire a respiratory signal of the subject of interest, the respiratory signal including a plurality of respiratory cycles;
      calculate a respiratory profile using the respiratory signal;
      for each respiratory cycle, generate a gating window, calculate a minimum total squared difference (TSD) between a plurality of phases in the respiratory profile and the same plurality of phases in the respiratory cycle, and position the gating window based on the TSD values calculated; and
      reconstruct a 3D image using only the emission data within the plurality of gating windows.

11. The imaging system of claim 10, wherein the emission data used to reconstruct the 3D image includes 50% or less of the acquired 3D emission dataset for each respiratory cycle, wherein the computer is further programmed to, for each respiratory cycle, position the gating window using information derived from an offset window.

12. The imaging system of claim 11, wherein the offset window further comprises a plurality of steps, the computer is further programmed to, for each respiratory cycle, calculate a TSD value for each step in the offset window, and select the minimum TSD value, from the calculated TSD values.

13. The imaging system of claim 10, wherein the computer is further programmed to:
    generate an offset window;
    divide the offset window into a plurality of steps;
    determine a TSD for each of the plurality of steps; and
    positioning the gating window at the TSD having the minimum value.

14. The imaging system of claim 10, wherein the computer is further programmed to:
    generate an offset window;
    determine a plurality of TSDs within the offset window; and
    position a first side of the Rating window at the minimum TSD.

15. The imaging system of claim 10, wherein the computer is further programmed to:
    generate a plurality of respiratory cycles; and
    calculate a mean value of the plurality of respiratory cycles.

16. The imaging system of claim 10, wherein the plurality of gating windows includes only a single gating window from each respiratory cycle, and wherein, for each respiratory cycle, the single gating window has a first side, a second side, and a width, the width being less than a length of the respiratory cycle.

17. A non-transitory computer readable medium encoded with a program programmed to instruct a computer to:
    acquire a 3D emission dataset of the subject of interest;
    acquire a respiratory signal of the subject of interest, the respiratory signal including a plurality of respiratory cycles;
    calculate a respiratory profile using the respiratory signal;

for each respiratory cycle, generate a gating window, calculate a minimum total squared difference (TSD) between a plurality of phases in the respiratory profile and the same plurality of phases in the respiratory cycle, and position the gating window such that the TSD is minimized; and reconstruct a 3D image using only the emission data within the plurality of gating windows.

18. The non-transitory computer readable medium of claim 17, further programmed to instruct a computer to position the gating window using information derived from an offset window, wherein the emission data used to reconstruct the 3D image includes 50% or less of the acquired 3D emission dataset for each respiratory cycle.

19. The non-transitory computer readable medium of claim 18, further programmed to instruct a computer to:

divide the offset window into a plurality of steps;

calculate a TSD value for each step in the offset window; and select the minimum TSD value from the calculated TSD values.

20. The non-transitory computer readable medium of claim 18, further programmed to instruct a computer to:

generate an offset window;

determine a plurality of TSDs within the offset window; and position a first side of the gating window at the minimum TSD.

* * * * *

UNITED STATES PATENT AND TRADEMARK OFFICE
CERTIFICATE OF CORRECTION

PATENT NO.       : 9,078,622 B2  
APPLICATION NO.  : 13/800187  
DATED            : July 14, 2015  
INVENTOR(S)      : Scott David Wollenweber et al.

Page 1 of 1

It is certified that error appears in the above-identified patent and that said Letters Patent is hereby corrected as shown below:

On the Title page, in item (54): Replace the word "TOMOGRPAHY" with "TOMOGRAPHY"

Signed and Sealed this  
Seventeenth Day of November, 2015

Michelle K. Lee  
*Director of the United States Patent and Trademark Office*